(12) United States Patent
Chu et al.

(10) Patent No.: US 6,797,344 B2
(45) Date of Patent: Sep. 28, 2004

(54) AROMATIC DIAMINE DERIVATIVES, THE PREPARATION THEREOF AND ALIGNMENT FILM MATERIALS CONTAINING SAME FOR LIQUID CRYSTAL DISPLAY CELL

(75) Inventors: Wen-Chung Chu, Chiautou Shiang (TW); Shih-Chieh Yeh, Yanchau Shiang (TW); Chia-Wen Chang, Taichung (TW)

(73) Assignee: Eternal Chemical Co., Ltd., Kaohsiung (TW)

( * ) Notice: Subject to any disclaimer, the term of this patent is extended or adjusted under 35 U.S.C. 154(b) by 0 days.

(21) Appl. No.: 10/659,589

(22) Filed: Sep. 10, 2003

(65) Prior Publication Data

US 2004/0084653 A1 May 6, 2004

(30) Foreign Application Priority Data

Sep. 11, 2002 (CN) ...................................... 091120720 A

(51) Int. Cl.$^7$ ....................... C09K 19/56; C07C 211/51; C08G 73/10
(52) U.S. Cl. ................... 428/1.26; 252/299.4; 564/307; 564/347; 528/170; 528/179; 528/185
(58) Field of Search .................... 252/299.4; 428/1.26; 564/307, 347; 528/170, 179, 185

(56) References Cited

U.S. PATENT DOCUMENTS 6,111,059 A     8/2000   Nihira et al. ................ 528/353
6,500,913 B2 * 12/2002  Mathew et al. ............. 528/170

FOREIGN PATENT DOCUMENTS

| CN | 244953      | 4/1995  |
| EP | 0 604 885 A1 | 7/1994 |
| JP | 05313169    | 11/1993 |
| JP | 07-287235   | 10/1995 |

* cited by examiner

*Primary Examiner*—Shean C. Wu
(74) *Attorney, Agent, or Firm*—Scully, Scott, Murphy & Presser

(57) ABSTRACT

New aromatic diamine derivatives and the preparation thereof are disclosed. The diamine derivatives of the present invention can be added to conventional polymerization reactions of tetracarboxylic acids or dianhydrides thereof and diamines to form new polyamic acids. After high-temperature baking, the polyamic acids are cyclized to form polyimides. These polyimides can be used as alignment film materials for liquid crystal display cell and have good alignment property and stability, and are effective in promoting pre-tilt angles.

12 Claims, No Drawings

AROMATIC DIAMINE DERIVATIVES, THE PREPARATION THEREOF AND ALIGNMENT FILM MATERIALS CONTAINING SAME FOR LIQUID CRYSTAL DISPLAY CELL

BACKGROUND OF THE INVENTION

(1) Field of the Invention

The present invention relates to new aromatic diamine monomer derivatives and to alignment film materials containing the diamine monomer derivatives for liquid crystal displays (LCDs). The alignment film materials are effective in allowing the liquid crystal molecules positioned between two substrates to have stable, high tilt angles.

(2) Description of the Prior Art

LCD is a liquid crystal photo-electric conversion device, which has advantages of having small size, lightweight, low power consumption, and good display quality, and has become more popular in the field of flat panel display in recent years.

A LCD device typically comprises a display element of twisted nematic (TN) type liquid crystal materials, which responds to electric fields and contain liquid crystal molecules having positive dielectric anisotropy. Normally, the liquid crystal molecules are positioned between a pair of substrates having electrodes, and the alignment directions of the substrates are perpendicular to each other. The alignments of the liquid crystal molecules are controlled by an electric field. For TN type LCDs, it is important to obtain uniform tilt angles between the long axes of the liquid crystal molecules and the inside surfaces of the substrates. The materials utilized to align liquid crystal molecules to have uniform pre-tilt angles are called alignment films.

There are two typical methods for preparing alignment films in industry.

In the first method, an inorganic film is formed from an inorganic material by vapor deposition. For example, a silicon dioxide film can be formed on a substrate by tilt vapor deposition. The liquid crystal molecules are aligned to the direction of the vapor deposition. This method allows the liquid crystal molecules to have a uniform alignment, but is not beneficial to industry.

The second method pertains to coating an organic film on the surface of a substrate and rubbing the coated surface by cotton cloth, nylon, or polyester fabric to align the surface of the organic film such that the liquid crystal molecules can be oriented to the rubbing direction. By this method, it is also easy to obtain uniform alignment. Due to the simplicity of this method, it is more suitable for industry-scale productions. Polymers which can be formed into organic films include, for example, polyvinyl alcohols, polyethylene oxides, polyamides, and polyimides, of which polyimides are the preferred ones due to their good chemical and thermal stabilities.

For different applications, the alignment film materials can be used in TN type, super-twisted nematic (STN) type, or thin film transistor (TFT) type LCDs. In addition to orientation ability and good coating properties, the pre-tile angle is also important for an alignment film. There are many documented methods for controlling the pre-tilt angle. For example, EP 0 604 885 A1 discloses utilizing siloxane copolymer materials as alignment film materials and controlling the pre-tilt angle of the alignment film by adjusting the amount of the siloxane. Nevertheless, the materials are merely suitable for wide viewing STN and TFT LCDs. JP 05313169-A discloses a method of controlling the tilt angle of an alignment film by controlling the degree of ring-closing reaction of a polyamic acid solution to form a polyimide. Nevertheless, the method is merely suitable for high pre-tilt angles. JP 07287235-A discloses a method of using a polyimide having a straight chain alkyl group at an end of the polyimide and a polyamic acid having an aliphatic tetracarboxylic acid structure in an alignment film to increase the pre-tilt angle of the alignment film. Nevertheless, this method is only suitable for STN LCD.

The tilt angle obtained by rubbing a polyimide resin is normally in the range from about 1° to 3° and it is difficult to obtain higher angles. In order to solve this problem, Japanese Laid-Open Patent Application No. 9-278724/1997 discloses a polyimide resin alignment film comprising a cyclohexane side chain containing a carbonaceous straight chain alkyl. Although the pre-tilt angle of the alignment film can be widely controlled, the cost for preparing the diamine monomers is high.

In order to obviate the above-mentioned drawbacks, the inventors of the application have developed new aromatic diamine monomer derivatives, which is useful in an alignment film to provide excellent orientation and stable and high tilt angles.

SUMMARY OF THE INVENTION

It is an object of the present invention to provide a new aromatic diamine monomer derivative.

It is another object of the present invention to provide a method for preparing the aromatic diamine monomer derivative.

It is still another object of the present invention to provide an alignment film material containing the aromatic diamine monomer derivative for a liquid crystal display (LCD).

DETAILED DESCRIPTION OF THE INVENTION

The aromatic diamine monomer derivative according to the present invention has the structure of formula (I):

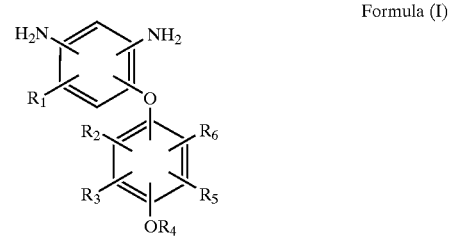

Formula (I)

wherein,
each of $R_1$, $R_2$, $R_3$, $R_5$, and $R_6$, independently, is hydrogen or a monovalent organic functional group, and
$R_4$ is $C_4$–$C_{20}$ alkyl, $CO_2R_7$, $CONR_7$, or $(CH_2)_nCF_3$, wherein n is an integer of from 1 to 5, and $R_7$ is $C_4$–$C_{20}$ alkyl.

In formula (I), preferably, each of $R_1$, $R_2$, $R_3$, $R_5$, and $R_6$, independently, is hydrogen, $C_1$–$C_5$ alkyl, $R_4$ is $C_4$–$C_{20}$ alkyl, and the two amino groups are directly attached to the 2-position and the 4-position of the benzene ring. In a preferred embodiment of the present invention, the compound of formula (I) can be 1-[4-(2,4-diaminophenoxy)phenoxy]octane or 1-[4-(2,4-diaminophenoxy)phenoxy]dodecane.

Typically, the aromatic diamine monomer derivatives of formula (I) of the present invention can be synthesized according to the following scheme:

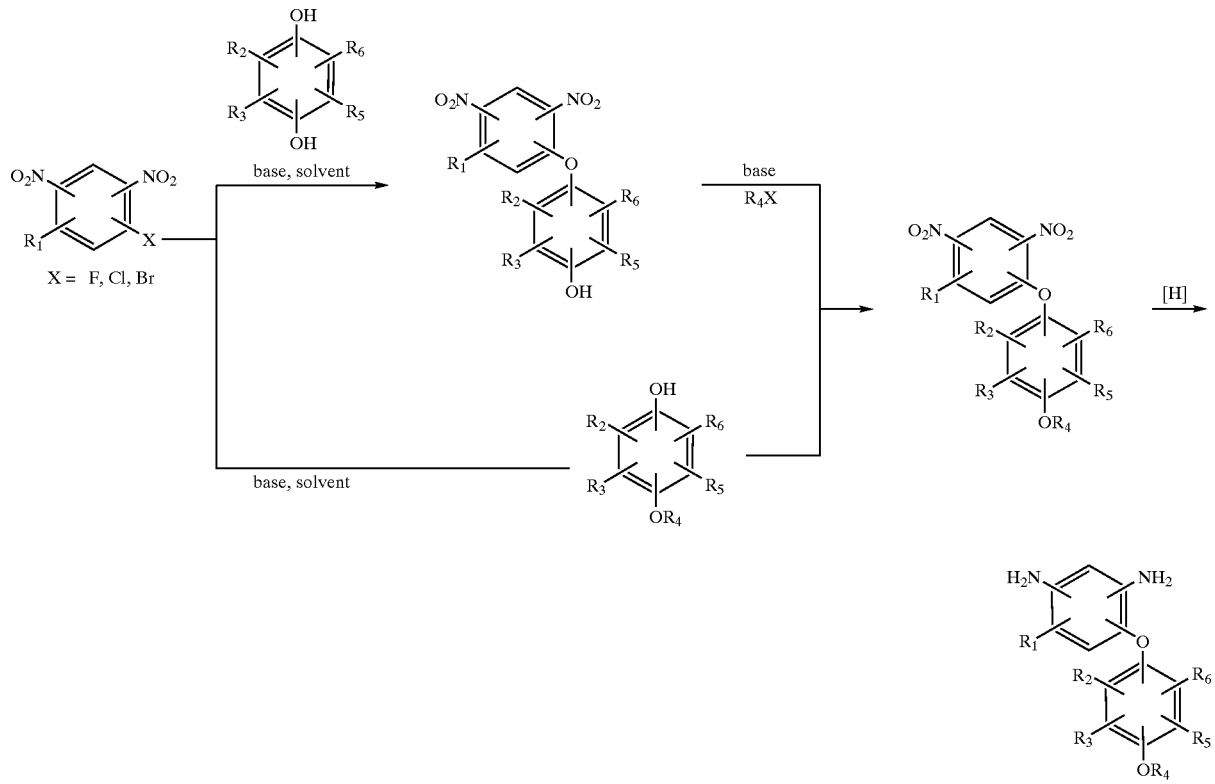

Therefore, the present invention also provides a method for preparing the aromatic diamine monomer derivatives of formula (I), the method comprising:

(a) reacting a dinitrobenzene compound of formula (II)

Formula (II)

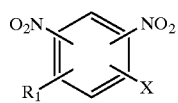

with a hydroquinone compound of formula (III)

Formula (III)

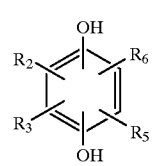

in the presence of a base and an organic solvent to form a compound of formula (IV);

Formula (IV)

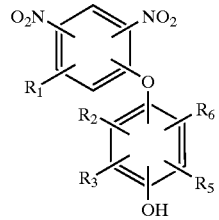

(b) reacting the compound of formula (IV) with a halide $R_4X$ in the presence of a base and an organic solvent to form a compound of formula (V), Formula (V)

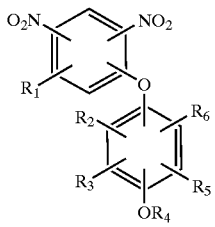

and
(c) hydrogenating the compound of formula (V) to form the compound of formula (I).

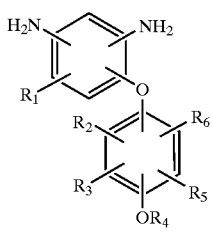

Formula (I)

In the compounds of formula (I) to formula (V), $R_1$, $R_2$, $R_3$, $R_4$, $R_5$, and $R_6$ are defined as aforementioned, and X is a halogen selected from the group consisting of F, Cl, and Br.

As used hereinbefore, the term "monovalent organic functional group" refers to an organic functional group having single bonding, which includes, but not limited to, substituted or unsubstituted $C_1$–$C_{20}$ alkyl, preferably $C_1$–$C_5$ alkyl.

As used hereinbefore, the term "alkyl" refers to straight or branched, saturated hydrocarbon chain of from 1 to 20 carbon atoms, which includes, but not limited to, methyl, ethyl, propyl, butyl, pentyl, hexyl, heptyl, octyl, nonyl, decyl, dodecyl, and the like.

In the above method for preparing the inventive diamine monomer derivatives, the base added to the reactions is used as a catalyst to speed-up the reactions and lower the reaction temperatures. Suitable bases include, but not limited to, the alkaline compounds of IA and IIA metals, preferably the carbonates of IA and IIA metals, and tertiary amines, preferably trimethylamine, triethylamine, diisopropylethylamine, and the like. The organic solvent suitable for the synthesis method includes, but is not limited to, acetone, butanone, N-methylpyrrolidone (NMP), N,N-dimethylacetamide (DMAC), N,N-dimethylformamide (DMF), and the like. The halides suitable for the synthesis method preferably are $C_4$–$C_{20}$ alkyl fluoride, chloride, and bromide.

The above-mentioned reduction reaction (hydrogenation) can be performed by any conventionally known hydrogenation method. For instance, the hydrogenation can be performed by hydrogen in the presence of Pt, Pd, or Raney-Ni as the catalyst and at suitable pressures and temperatures; or the reduction can be performed in concentrated hydrochloric acid by utilizing $SnCl_2$ or Fe as the reducing agent; or the reduction is performed in an aprotic solvent by utilizing $LiAlH_4$ as the reducing agent.

The present invention further provides alignment film materials for orienting liquid crystal molecules. The alignment film materials comprise a polyimide resin obtained from the inventive diamine monomer derivatives of formula (I). The resin can be prepared by any conventionally known methods, and by the polymerization reaction of a conventional tetracarboxylic acid or an anhydride thereof, a conventional diamine monomer, and one or more of the inventive diamine monomer derivatives of formula (I). The resultant polyimide resin will dissolve in polar organic solvents, such as N-methylpyrrolidone, N,N-dimethylacetamide, or γ-butyrolactone, to form a polyimide solution. The solution is coated on a glass or a plastic transparent substrate having transparent electrodes. Then, the solvent is thermally evaporated by heating the substrate at 120 to 350° C. to form a polyimide resin film on the substrate. Finally, the film is rubbed and oriented to form an alignment film, which will allow liquid crystal molecules to have stable and high pre-tilt angles.

The conventional tetracarboxylic acids which can be used in the present invention are not limited and include aromatic tetracarboxylic acids, such as 1,2,4,5-benzene tetracarboxylic acids, 3,3',4,4'-diphenyl tetracarboxylic acids, 2,3,3',4-diphenyl tetracarboxylic acids, bis(3,4-dicarboxylphenyl) ether, 3,3',4,4'-benzophenone tetracarboxylic acids, bis(3,4-dicarboxylphenyl)sulfoxide, bis(3,4-dicarboxylphenyl) methane, 2,2-bis(3,4-dicarboxylphenyl)propane, 1,1,1,3,3,3,-hexafluoro-2,2-bis(3,4-dicarboxylphenyl)propane, bis(3,4-dicarboxylphenyl)dimethylsilane, bis(3,4-dicarboxylphenyl)diphenylsilane, 2,3,4,5-pyridine tetracarboxylic acid, and 2,6-bis(3,4-dicarboxylphenyl) pyridine, and dianhydrides and dicarboxylic diacyl halide derivatives of the above-mentioned compounds; cycloaliphatic tetracarboxylic acids, such as cyclobutane tetracarboxylic acids, cyclohexane tetracarboxylic acids, cyclopentane tetracarboxylic acids, and 1,3,5-tricarboxylcyclopentane acetic acid, and 3,4-dicarboxyl-1,2,3,4-tetrahydrogen-1-naphthyl succinic anhydride, and dianhydrides and dicarboxylic diacyl halide derivatives of the above-mentioned compounds; and aliphatic tetracarboxylic acids, such as butane tetracarboxylic acids, and the dianhydride and dicarboxylic diacyl halide derivatives thereof. The tetracarboxylic acids can be used alone or two or more of the acids can be used in combination in the present invention.

The conventional diamine components which can be used in the present invention are typically the primary diamines for the synthesis of polyamic acids. These diamine components can be aromatic diamines, which include, but not limited to, diamino diphenyl methane, diamino diphenyl ether, 2,2-diaminophenyl propane, bis(3,5-diethyl-4-aminophenyl)methane, diamino diphenyl sulfone, diaminobenzophenone, diaminonaphthalene, 1,4-bis(4-aminophenoxy)benzene, 1,3-bis(4-aminophenoxy)benzene, 4,4-bis(4-aminophenoxy)diphenyl sulfone, 2,2-bis(4,4-aminophenoxyphenyl)propane, 2,2-bis(4-aminophenyl) hexafluoropropane, and 2,2-bis(4,4-aminophenoxyphenyl) hexafluoropropane; aliphatic cyclicdiamines such as bis(4-aminocyclohexyl)methane, and bis(4-amino-3-methylcyclohexyl)methane; and aliphatic diamines such as butylene diamine and hexamethylene diamine. The above-mentioned diamine compounds can be used alone or two or more of the compounds can be used together.

The diamine components used in the present invention must include at least one of the diamine monomer derivatives of formula (I) of the present invention. The amount of the diamine monomer derivative of formula (I), on the basis of the total amount of the diamines used, is normally at least 5 mol %, preferably at least 20 mol %, and more preferably at least 50 mol %.

As for the polymerization reaction of the polyimide, a preferred degree of polymerization (DP) of the product refers to a reduced viscosity of the product solution ranging from 0.05 to 3.0 dl/g, as measured at the temperature of 30° C. with the concentration of N-methylpyrrolidone being 0.5 g/dl.

There are no particular limitations regarding the reaction or polymerization between the tetracarboxylic acids or the dianhydride derivatives thereof and the diamines. The reaction or polymerization can be performed by any conventionally known methods. In a commonly used method, a diamine is dissolved in a polar organic solvent, such as N-methylpyrrolidone, N,N-dimethylacetamide, or N,N-dimethylformamide, or the mixture thereof, and then a tetracarboxylic acid or a dianhydride derivative thereof is added into the solution to form a polyamic acid solution. The reaction temperature is in the range from –20 to 150° C., preferably from –5 to 100° C. The polymerization time normally ranges from 3 minutes to 24 hours, preferably from 10 minutes to 6 hours.

In the inventive alignment film materials, the molar ratio between the tetracarboxylic acids and dianhydride derivatives thereof and the diamines is adjusted to be in the range from 0.8 to 1.2, so that the resultant polyamic acids would have suitable molecular weight distribution and strength. When the molar ratio between the tetracarboxylic acids or the dianhydride derivatives thereof and the diamines is near 1, the resultant polymer will have higher molecular weights and viscosity. When the molar ratio between the tetracarboxylic acids or the dianhydride derivatives thereof and the diamines is less than 1, a proper amount of end cap functional groups can be added to the reaction to compensate the difference in the molar ratio so as to reduce the oxidation reaction caused by the difference. Suitable end cap functional groups may derived from phthalic anhydride, maleic anhydride, aniline, and cyclohexylamine, and the like.

Additionally, a catalyst can be added in the polymerization reaction to increase the DP and reduce the reaction time. Suitable catalysts include, but not limited to, triethylamine, diethylamine, n-butyl amine, and pyridine. The catalysts also provide advantages of adjusting the pH value of the solution.

The DP of the polyamic acids obtained by the polymerization reaction is in the range from 10 to 5,000, preferably 16 to 250. The average weight molecular weight of the polyamic acids is in the range from 5,000 to 2,500,000, more suitably from 8,000 to 125,000.

The solids content of the polyamic acid product (i.e. the weight percentage of the polymer relative to the solvent) is in the range from 10% to 30%. However, for practical applications, the solids content should be reduced to 4% to 10% to alter the viscosity and control the film thickness.

In order to improve the adhesion of the alignment film materials of the polyamic acid resin to the substrate, a minor amount of additives, such as silane coupling agents, can be added to the resin. Commonly used silane coupling agents include, but not limited to, 3-aminopropyl trimethoxysilane, 3-aminopropyl triethoxysilane, 2-aminopropyl trimethoxysilane, 2-aminopropyl triethoxysilane, and mixtures thereof.

As mentioned above, for practical applications, the polyamic acid product should be diluted with organic solvents to have a solids content of from 4% to 10% by weight, so as to facilitate the subsequent processings of the alignment film. Suitable organic solvents include N-methylpyrrolidone, m-cresol, γ-butyrolactone, N,N-dimethylacetamide, N,N-dimethylformamide, and mixtures thereof. However, it is possible to use a solvent that does not have ability to dissolve the polyamic resin may also be used only if it will not adversely affect the solubility of the polyamic resin in the whole solvent system. Such solvents include, but not limited to, ethylene glycol monoethyl ether, ethylene glycol monobutyl ether, diethylene glycol monobutyl ether, diethylene glycol monoethyl ether, butyl carbitol, ethyl carbitol acetate, or ethylene glycol, or mixtures thereof. The amount of such solvents should be controlled to be less than 90% by weight of the total weight of the whole solvent system.

To convert the polyamic acid resin to the corresponding polyimide resin, the polyamic acids are heated, dehydrated, and cyclized to form the polyimide resin. The heating temperature is between 100° C. to 350° C. Suitable temperatures for the cyclization reaction are in the range from 120° C. to 320° C. The duration time for the cyclization reaction is between 3 minutes and 6 hours.

The present invention provides alignment film materials, which will align liquid crystal molecules to have high pre-tilt angles. The alignment film materials can be coated uniformly on a substrate by commercially available coating means, such as a scraper coating, a spin coating, or a roller coating. In the coating method, the polyimide resin thin film having a thickness of between 200 Å and 3000 Å is formed on a transparent substrate, such as a glass substrate or a plastic substrate with transparent electrodes and, then, the polyimide resin thin film is rubbed and oriented to form a liquid crystal alignment film.

To ascertain that the new alignment film materials of the present invention can form an alignment film with high pre-tilt angles, a liquid crystal cell is prepared for the determination of the pre-tilt angle property of the inventive alignment film materials. The preparation of a liquid crystal cell comprises providing and cleaning two indium tin oxide (ITO) glass substrates, and then the inventive alignment film materials are coated onto the substrates. The coating method includes scraper coating, spinning coating or roller coating. After pre-baking and high-temperature baking, a polyimide alignment film is formed on the substrates. Thereafter, the substrates are cooled, and the alignment films are rubbed and oriented by a brush, and then the substrates are assembled to form the liquid crystal cell. After injecting liquid crystal, a tilt angle tester is utilized to determine the pre-tilt angle of the alignment film of the present invention.

The present invention will be further described in the following examples. While the invention has been particularly shown and described with the reference to the preferred embodiments thereof, the embodiments will not make any limitations to the scope of the invention. Any modifications or alterations on the invention that can be easily accomplished by persons skilled in the art are encompassed in the disclosure of the specification and the accompanying claims.

EXAMPLES

Synthesis of Aromatic Diamine Compounds

Example 1

Synthesis of 1-[4-(2,4-diaminophenoxy)phenoxy]octane (DPP-8)

In a 500 ml 2-necked bottle equipped with a condenser tube, butanone (200 ml), and then 2,4-dinitrofluorobenzene (18.60 g, 0.100 mol), hydroquinone (11.32 g, 0.100 mol), and potassium carbonate (15.26 g, 0.110 mol) were introduced. The mixture were agitated at room temperature for 2 hours. Then, potassium carbonate (15.26 g, 0.110 mol), octane bromide (27.41 g, 0.110 mol), and butanone (20 ml) were added to the bottle. The mixture were stirred at room temperature for 6 hours. Thereafter, distilled water (300 ml) was added to the bottle, and the mixture was extracted by ethyl acetate (300 ml×3). The collected organic layers were dried by anhydrous sodium sulfate, filtered, and concentrated, and recrystallized by ethanol to obtain 1-[4-(2,4-dinitrophenoxy)phenoxy]octane (31.08 g, 0.080 mol). Yield: 80%. Spectrum: IR (KBr) 3096, 2938, 2854, 1604, 1526, 1504, 1476, 1348, 1273, 1240, 1188, 1116, 1069, 1001 cm$^{-1}$. $^1$HNMR (DMSO-d$_6$, 300 MHz). δ8.88 (d, J=2.8 Hz, 1H), 8.43 (dd, J=2.8, J=9.3 Hz, 1H), 7.21 (d, J=8.6 Hz, 2H), 7.10~7.05 (m, 3H), 3.98 (t, J=6.4 Hz, 2H), 1.73 (quintet, J=6.7 Hz, 2H), 1.4~1.2 (m, 10H), 0.87 (t, J=6.2, 3H) $^{13}$C NMR (DMSO-d$_6$, 75 MHz). δ57.0, 156.1, 146.6, 141.0, 139.0, 129.7, 122.1, 122.0, 118.3, 116.3, 68.1, 31.5, 29.0, 28.9, 28.8, 25.7, 22.3, 14.1.

The resultant 1-[4-(2,4-dinitrophenoxy)phenoxy]octane (31.08 g, 0.080 mol) and ethanol (700 ml) and 10% Pd/C (1.50 g) were introduced into a 2-liter (l) reaction bottle.

After hydrogen passed through the reaction under normal pressure for 4 hours, the reaction mixture was filtered and concentrated to obtain a crude product. The crude product was recrystallized by ethanol to obtain 1-[4-(2,4-diaminophenoxy)phenoxy]octane (22.33 g, 0.068 mol). Yield: 85%. Spectrum: IR (KBr) 3420, 3352, 2924, 2856, 1618, 1503, 1466, 1215, 1105, 1027 cm$^{-1}$, $^1$H NMR (DMSO-d$_6$, 300 MHz). δ0.8~6.7 (m, 4H), 6.46 (d, J=8.3 Hz, 1H), 6.02 (d, J=2.0 Hz, 1H), 5.79 (dd, J=8.5, J=2.2 Hz, 1H), 4.61 (s, 2H), 4.47 (s, 2H), 3.82 (t, J=5.7 Hz, 2H), 1.70~1.50 (m, 2H), 1.40~1.10 (m, 10H), 0.84 (t, J=6.1 Hz, 3H). $^{13}$C NMR (DMSO-d$_6$, 75 MHz). δ153.5, 152.7, 151.3, 146.1, 140.9, 133.4, 121.4, 116.8, 115.3, 103.2, 101.6, 68.0, 31.5, 29.0, 28.9, 25.7, 22.3, 14.1

Example 2

Synthesis of 1-[4-(2,4-diaminophenoxy)phenoxy]dodecane (DPP-12)

In a 500 ml 2-necked bottle equipped with a condenser tube, butanone (200 ml), and then 2,4-dinitrofluorobenzene (18.61 g, 0.100 mol), hydroquinone (11.33 g, 0.100 mol), and potassium carbonate (15.28 g, 0.110 mol) were introduced. The mixture were agitated at room temperature for 2 hours. Then, potassium carbonate (15.27 g, 0.110 mol), dodecane bromide (15.26 g, 0.110 mol), and butanone (20 ml) were added to the bottle. The mixture were stirred at room temperature for 6 hours. Thereafter, distilled water (300 ml) was added to the bottle, and the mixture was extracted by ethyl acetate (300 ml×3). The collected organic layers were dried by anhydrous sodium sulfate, filtered, and concentrated, and recrystallized by ethanol to obtain 1-[4-(2,4-dinitrophenoxy)phenoxy]dodecane (35.58 g, 0.080 mol). Yield: 80%. Spectrum: IR (KBr) 3121, 3088, 2918, 2853, 1611, 1530, 1470, 1350, 1287, 1159, 1097, 1075 cm$^{-1}$. $^1$H NMR (DMSO-d$_6$, 300 MHz). δ8.84 (d, J=2.5 Hz, 1H), 8.40 (dd, J=2.5, J=9.3 Hz, 1H), 7.17 (d, J=8.9 Hz, 2H), 7.03 (t, J=9.9 Hz, 3H), 3.94 (t, J=6.4 Hz, 2H), 1.70 (quintet, J=6.8 Hz, 2H), 1.4~1.2 (m, 18H), 0.83 (t, J=6.0, 3H) $^{13}$C NMR (DMSO-d$_6$, 75 MHz) δ157.0, 156.1, 146.5, 141.0, 139.0, 129.6, 121.9, 118.3, 116.2, 68.2, 68.1, 31.5, 29.2, 29.0, 28.9, 25.7, 22.3, 14.0.

The resultant 1-[4-(2,4-dinitrophenoxy)phenoxy]dodecane (35.58 g, 0.080 mol) and ethanol (700 ml) and 10% Pd/C (1.78 g) were introduced into a 2-liter (l) reaction bottle. After hydrogen passed through the reaction under normal pressure for 4 hours, the reaction mixture was filtered and concentrated to obtain a crude product. The crude product was recrystallized with ethanol to obtain 1-[4-(2,4-diaminophenoxy)phenoxy]dodecane (26.15 g, 0.068 mol). Yield: 85%. Spectrum:IR (KBr) 3412, 3333, 2923, 2850, 1614, 1515, 1462, 1366, 1219, 1084 cm$^{-1}$. $^1$H NMR (DMSO-d$_6$, 300 MHz). δ6.8~6.7 (m, 4H), 6.45 (d, J=8.3, 1H), 6.02 (d, J=2.2 Hz, 1H), 5.79 (dd, J=8.4, J=2.4 Hz, 1H), 4.61 (s, 2H), 4.47 (s, 2H), 3.81 (t, J=6.3 Hz, 2H), 1.75~1.55 (m, 2H), 1.40~1.10 (m, 18H), 0.82 (t, J=6.3 Hz, 3H). $^{13}$C NMR (DMSO-d$_6$, 75 MHz)δ 153.5, 152.7, 146.1, 140.9, 133.4, 121.4, 116.8, 115.3, 103.2, 101.5, 68.0, 31.5, 29.2, 29.0, 28.9, 25.7, 22.3, 14.1.

Synthesis of Polyimide and Preparation of Alignment Film

Example 3

A mixture of 19.5 g (0.0475 mol) 2,2-bis[4-(4-aminopheoxy)phenyl]propane (BAPP), 0.82 g (0.0025 mol) 1-[4-(2,4-diaminophenoxy)phenoxy] (DPP-8), and 10.9 g (0.05 mol) 1,2,4,5-benzene dianhydride (PMDA) in 125 g N-methyl-2-pyrrolidone (NMP) was reacted at room temperature for 5 hours. Then, 468 g NMP was added to dilute the reaction to obtain a polyamic acid solution with a reduced viscosity of 1.10 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 3.6 as measured by Tilt Angle Tester.

Example 4

A mixture of 18.5 g (0.045 mol) BAPP, 1.64 g (0.005 mol) DPP-8, and 10.9 g (0.05 mol) PMDA in 124 g NMP was reacted at room temperature for 30 hours. Then, 466 g NMP was added to dilute the reaction to obtain a polyamic acid solution with a reduced viscosity of 1.00 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 4.6 as measured by Tilt Angle Tester.

Example 5

A mixture of 4.3 g (0.04 mol) BAPP, 3.3 g (0.01 mol) DPP-8, and 10.9 g (0.05 mol) PMDA in 74 g NMP was reacted at room temperature for 25 hours. Then, 278 g NMP was added to dilute the reaction to obtain a polyamic acid solution with a reduced viscosity of 0.90 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 6.8 as measured by Tilt Angle Tester.

Example 6

A mixture of 18.47 g (0.045 mol) BAPP, 1.64 g (0.005 mol) DPP-8, 5.4 g (0.05 mol) PMDA and 7.4 (0.025 mol) BPDA (3,3',4,4'-diphenyldianhydride) in 132 g NMP was reacted at room temperature for 20 hours. Then, 493 g NMP was added to dilute the reaction to obtain a polyamic acid solution with a reduced viscosity of 1.05 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 10.0 as measured by Tilt Angle Tester.

Example 7

A mixture of 19.5 g (0.0475 mol) BAPP, 0.96 g (0.0025 mol) 1-[4-(2,4-diaminophenoxy)phenoxy]dodecane (DPP-12), and 10.9 g (0.05 mol) PMDA in 125 g NMP was reacted at room temperature for 25 hours. Then, 471 g NMP was added to dilute the reaction to obtain a polyamic acid solution with a reduced viscosity of 1.10 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 4.3 as measured by Tilt Angle Tester.

Example 8

A mixture of 18.5 g (0.045 mol) BAPP, 1.92 g (0.005 mol)DPP-12, and 10.9 g (0.05 mol) PMDA in 125 g NMP was reacted at room temperature for 25 hours. Then, 470 g NMP was added to dilute the reaction to obtain a polyamic acid solution with a reduced viscosity of 0.90 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 5.6 as measured by Tilt Angle Tester.

Example 9

A mixture of 12.3 g (0.03 mol) BAPP, 7.69 g (0.02 mol) DPP-12, and 10.9 g (0.05 mol) PMDA in 124 g NMP was reacted at room temperature for 25 hours. Then, 463 g NMP was added to dilute the reaction to obtain a polyamic acid solution with a reduced viscosity of 0.60 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 15.0 as measured by Tilt Angle Tester.

Comparative Example 1

A mixture of 20.5 g (0.05 mol) BAPP and 10.9 g (0.05 mol) PMDA in 126 g NMP was reacted at room temperature for 15 hours. Then, 470 g NMP was added to dilute the reaction to obtain a polyamic acid solution with a reduced viscosity of 1.22 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 2.6 as measured by Tilt Angle Tester.

Comparative Example 2

A mixture of 20.5 g (0.05 mol) BAPP, 5.4 g (0.025 mol) PMDA, and 7.4 g (0.025 mol) BPDA in 133 g NMP was reacted at room temperature for 20 hours. Then, 500 g NMP was added to dilute the reaction to obtain a polyamic acid solution with a reduced viscosity of 1.15 dl/g. The polyamic acid solution is spin coated (at 3500 rpm) onto two glass substrates having transparent electrodes. The coatings were heated at 250° C. for 60 minutes to form polyimide resin films on the substrates. After cooling the substrates, the films were rubbed and oriented by a brush to form alignment films. Then, the two substrates were assembled to form a parallel liquid crystal cell by a 50-micrometer spacer agent. Finally, liquid crystal (ZL1-2293, manufactured by Merck Company) was injected between the two substrates. The cell rotated between crossed nicols. It is satisfactory to tell the lightness and darkness apart. The pre-tilt angle of the alignment film is 3.0 as measured by Tilt Angle Tester.

The results obtained from Examples 3 to 9 and Comparative Examples 1 and 2 are listed in Table 1.

TABLE 1

| Example No. | Diamine (mol %) | | | Dianhydride (mol %) | | Orientation | Pre-tilt angle |
| --- | --- | --- | --- | --- | --- | --- | --- |
| | BAPP | DPP-8 | DPP-12 | PMDA | BPDA | | |
| Ex. 3 | 95 | 5 | | 100 | | Good | 3.6 |
| Ex. 4 | 90 | 10 | | 100 | | Good | 4.6 |
| Ex. 5 | 80 | 20 | | 100 | | Good | 6.8 |
| Ex. 6 | 90 | 10 | | 50 | 50 | Good | 10.0 |
| Ex. 7 | 95 | | 5 | 100 | | Good | 4.3 |
| Ex. 8 | 90 | | 10 | 100 | | Good | 5.6 |
| Ex. 9 | 60 | | 40 | 100 | | Good | 15.0 |

TABLE 1-continued

| Example | Diamine (mol %) | | | Dianhydride (mol %) | | Orientation | Pre-tilt angle |
|---|---|---|---|---|---|---|---|
| No. | BAPP | DPP-8 | DPP-12 | PMDA | BPDA | | |
| Cex. 1 | 100 | | | 100 | | Acceptable | 2.6 |
| Cex. 2 | 100 | | | 50 | 50 | Acceptable | 3.0 |

The above results show that the addition of at least 5% of the aromatic diamine monomer derivatives of the present invention to the alignment film materials will obtain good orientation and raise the pre-tilt angle of the resultant alignment film.

What is claimed is:

1. An aromatic diamine derivative having the structure of formula (I):

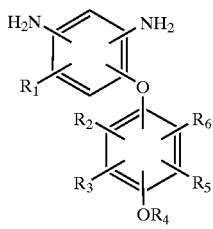

Formula (I)

wherein, each of $R_1$, $R_2$, $R_3$, $R_5$, and $R_6$, independently, is hydrogen or a monovalent organic functional group, and $R_4$ is $C_4$–$C_{20}$ alkyl, $CO_2R_7$, $CONR_7$, or $(CH_2)_nCF_3$, wherein n is an integer of from 1 to 5, and $R_7$ is $C_4$–$C_{20}$ alkyl.

2. The aromatic diamine derivative according to claim 1 wherein each of $R_1$, $R_2$, $R_3$, $R_5$, and $R_6$, independently, is hydrogen or $C_1$–$C_5$ alkyl, $R_4$ is $C_4$–$C_{20}$ alkyl, and the two amino groups are directly attached to the 2-position and the 4-position of the benzene ring.

3. The aromatic diamine derivative according to claim 1 wherein the aromatic diamine derivative is 1-[4-(2,4-diaminophenoxy)phenoxy]octane.

4. The aromatic diamine derivative according to claim 1 wherein the aromatic diamine derivative is 1-[4-(2,4-diaminophenoxy)phenoxy]dodecane.

5. A method for preparing the compound of formula (I) according to claim 1, the method comprising:

(a) reacting a dinitrobenzene compound of formula (II)

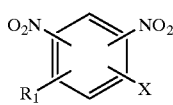

Formula (II)

with a hydroquinone compound of formula (III)

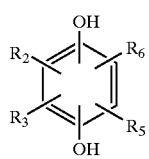

Formula (III)

in the presence of a base and an organic solvent to form a compound of formula (IV);

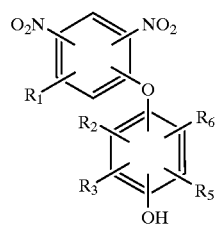

Formula (IV)

(b) reacting the compound of formula (IV) with a halide $R_4X$ in the presence of a base and an organic solvent to form a compound of formula (V);

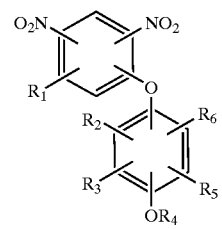

Formula (V)

and (c) hydrogenating the compound of formula (V) to form the compound of formula (I),

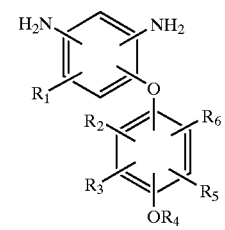

Formula (I)

wherein $R_1$, $R_2$, $R_3$, $R_4$, $R_5$, and $R_6$ are those defined in claim 1, and X is halogen selected from the group consisting of F, Cl, and Br.

6. The method according to claim 5 wherein the base is selected from the groups consisting of carbonates of IA and IIA metals, trimethylamine, triethylamine, and diisopropylethylamine.

7. The method according to claim 5 wherein the organic solvent is selected from the groups consisting of acetone, butanone, N-methylpyrrolidone, N,N-dimethylacetamide, and N,N-dimethylformamide.

8. The method according to claim 5 wherein the halide is selected from the groups consisting of $C_4$–$C_{20}$ alkyl fluoride, chloride, and bromide.

9. A polyimide resin used as an alignment film material for a liquid crystal display device, the polyimide resin being prepared by a polymerization reaction between a tetracarboxylic acid or a dianhydride derivative thereof and a diamine, wherein the diamine comprises at least 5 mol % of one or more of the diamine derivatives of formula (I) according to claim 1.

10. The polyimide resin according to claim 9 wherein the diamine comprises at least 20 mol % of one or more of the diamine derivatives of formula (I) according to claim 1.

11. The polyimide resin according to claim 9 wherein the diamine comprises 1-[4-(2,4-diaminophenoxy)phenoxy] octane.

12. The polyimide resin according to claim 9 wherein the diamine comprises 1-[4-(2,4-diaminophenoxy)phenoxy] dodecane.

* * * * *